United States Patent
Moghaddam

(10) Patent No.: US 9,029,086 B2
(45) Date of Patent: May 12, 2015

(54) DETECTION OF SINGLE AND MULTIMODAL ANALYTES

(76) Inventor: Masood Kamali Moghaddam, Knivsta (SE)

( * ) Notice: Subject to any disclaimer, the term of this patent is extended or adjusted under 35 U.S.C. 154(b) by 265 days.

(21) Appl. No.: 13/612,002

(22) Filed: Sep. 12, 2012

(65) Prior Publication Data

US 2013/0196316 A1    Aug. 1, 2013

Related U.S. Application Data

(60) Provisional application No. 61/590,860, filed on Jan. 26, 2012.

(51) Int. Cl.
*C12Q 1/68*    (2006.01)
*C07H 21/04*    (2006.01)
*G01N 33/53*    (2006.01)

(52) U.S. Cl.
CPC ............ *C12Q 1/6876* (2013.01); *C12Q 1/6804* (2013.01)

(58) Field of Classification Search
USPC ................................ 435/6.11, 7.11; 536/24.3
See application file for complete search history.

(56) References Cited

U.S. PATENT DOCUMENTS

2004/0219685 A1*    11/2004    Pappin et al. ................. 436/173

FOREIGN PATENT DOCUMENTS

| WO | WO 0161037 A1 | * | 8/2001 |
| WO | WO 2004057301 A2 | * | 7/2004 |
| WO | WO 2005123963 A2 | * | 12/2005 |
| WO | 2007/107743 A1 | | 9/2007 |

OTHER PUBLICATIONS

Medical Dictionary (retrieved on Jul. 7, 2014 from the internet: < http://medical-dictionary.thefreedictionary.com/analyte>).*
Darmanis et al. Molecular & Cellular Proteomics 9.2. 2010. 327-335.*
Darmanis et al. BioTechniques. 2007. 43: 443-450.*
Darmanis, Solid-Phase Proximity Ligation Assays, High-Performance Proximity Ligation Assays, Uppsala Universitet, Jan. 27, 2011.

(Continued)

*Primary Examiner* — Robert T Crow
*Assistant Examiner* — Joseph G Dauner
(74) *Attorney, Agent, or Firm* — Porter Wright Morris & Arthur LLP

(57) ABSTRACT

A method for detecting analyte in a sample comprises:

(a) contacting said sample with at least one set comprising a cassette oligonucleotide and first, second, third and fourth proximity probes, which probes each comprise an analyte-binding domain and a nucleic acid domain and can simultaneously bind to the analyte, the nucleic acid domains of said first and third proximity probes being complementary in a first overlap region and the nucleic acid domains of said second and fourth proximity probes being complementary in a second overlap region; and said cassette oligonucleotide being complementary to the nucleic acid domain of said third proximity probe in a third overlap region and to the nucleic acid domains of said fourth proximity probe in a fourth overlap region;

(b) allowing the overlap regions of said proximity probes and said cassette oligonucleotide to hybridise; and (c) detecting said hybridisation.

A kit is for performing the method.

19 Claims, 9 Drawing Sheets

(56) References Cited

OTHER PUBLICATIONS

Tavoosidana et al, Multiple Recognition Assay Reveals Prostasomes as Promising Plasma Biomarkers for Prostate Cancer, Proceedings of the National Academy of Sciences, 108(21):8809-8814 (May 9, 2011). PNAS Early Edition, pp. 1-6.

Holliger et al, Engineered Antibody Fragments and the Rise of Single Domains, Nature Biotechnology, vol. 23, No. 9, 2005, p. 1126-1136.

Carlsson et al, Characteristics of Human Prostasomes Isolated From Three Different Sources, The Prostate 54:322-330 (2003).

Nilsson et al, Immunization of mice and rabbits by intrasplenic deposition of nanogram quantities of protein attached to Sepharaose beads or nitrocellulose paper strips, J. Immunol Methods, 1987 4:99(1), p. 67-75 (Abstract only).

Darmanis et al, Sensitive Plasma Protein Analysis by Microparticle-based Proximity Ligation Assays, Molecular & Cellular Proteomics, 2010, 9:327-335 (first published Nov. 27, 2009).

Nilsson et al, Monoclonal Antibodies Against Human Prostasomes, The Prostate 35:178-184 (1998).

Ericsson et al, A Dual-Tag Microarray platform for high-performance nucleic acid and protein analyses, Nucleic Acid Research 2008, vol. 36, No. 8, e45, pp. 1-9.

Renneberg et al, Immunohistochemistry of a prostate membrane specific protein during development and maturation of the human prostate, J. Anat (1997) 190, p. 343-349.

Fredriksson et al, Protein Detection Using Proximity-Dependent DNA ligation assays, Nature Biotechnology, vol. 20, 2002, p. 473-477.

Ronquist et al, Prostatic origin of fucosyl transferase in human seminal-plasma—a study on healthy controls and on men with infertility or with prostatic cancer, Urol. Res, 1984, 12(5):243-247 (Abstract only).

Gullberg et al, Cytokine detection by antibody-based proximity ligation, Proceedings of the National Academy of Sciences, Jun. 2004, vol. 101, No. 22, p. 8420-8424.

* cited by examiner

SEQUENCE LISTING

```
<160> NUMBER OF SEQ ID NOS: 15

<210> SEQ ID NO 1
<211> LENGTH: 59
<212> TYPE: DNA
<213> ORGANISM: Artificial Sequence
<220> FEATURE:
<221> NAME/KEY: source
<222> LOCATION: 1..59
<223> OTHER INFORMATION: /organism="Artificial Sequence"
      /note="PLA probe"
      /mol_type="unassigned DNA"

<400> SEQUENCE: 1
cgcatcgccc ttggactacg actgacgaac cgctttgcct gactgatcgc taaatcgtg      59

<210> SEQ ID NO 2
<211> LENGTH: 61
<212> TYPE: DNA
<213> ORGANISM: Artificial Sequence
<220> FEATURE:
<221> NAME/KEY: source
<222> LOCATION: 1..61
```

```
<223> OTHER INFORMATION: /organism="Artificial Sequence"
      /note="PLA probe"
      /mol_type="unassigned DNA"

<400> SEQUENCE: 2
tcgtgtctaa agtccgttac cttgattccc ctaaccctct tgaaaaattc ggcatcggtg    60
a                                                                    61

<210> SEQ ID NO 3
<211> LENGTH: 61
<212> TYPE: DNA
<213> ORGANISM: Artificial Sequence
<220> FEATURE:
<221> NAME/KEY: source
<222> LOCATION: 1..61
<223> OTHER INFORMATION: /organism="Artificial Sequence"
      /note="PLA probe"
      /mol_type="unassigned DNA"

<400> SEQUENCE: 3
tagctaaggc ttagattatt attcttcttc ttcagtgcag gatcacgatt tagatatttt    60
t                                                                    61

<210> SEQ ID NO 4
<211> LENGTH: 64
<212> TYPE: DNA
<213> ORGANISM: Artificial Sequence
<220> FEATURE:
<221> NAME/KEY: source
<222> LOCATION: 1..64
<223> OTHER INFORMATION: /organism="Artificial Sequence"
      /note="PLA probe"
      /mol_type="unassigned DNA"

<400> SEQUENCE: 4
atattttctt tagacacgag tagcatacct tccccttctc tactactcct tcacctcctc    60
cact                                                                 64

<210> SEQ ID NO 5
<211> LENGTH: 53
<212> TYPE: DNA
<213> ORGANISM: Artificial Sequence
<220> FEATURE:
<221> NAME/KEY: source
<222> LOCATION: 1..53
<223> OTHER INFORMATION: /organism="Artificial Sequence"
      /note="PLA probe"
      /mol_type="unassigned DNA"

<400> SEQUENCE: 5
ctgcatgacg ctagctgaca ttttttgtca gctagcgtca tgcagcacga aaa           53

<210> SEQ ID NO 6
<211> LENGTH: 55
<212> TYPE: DNA
<213> ORGANISM: Artificial Sequence
<220> FEATURE:
<221> NAME/KEY: source
<222> LOCATION: 1..55
<223> OTHER INFORMATION: /organism="Artificial Sequence"
      /note="PLA probe"
      /mol_type="unassigned DNA"

<400> SEQUENCE: 6
tttcacgata cgtagacttc ggattcagtt ttttactgaa tccgaagtct acgta         55
```

-continued

```
<210> SEQ ID NO 7
<211> LENGTH: 59
<212> TYPE: DNA
<213> ORGANISM: Artificial Sequence
<220> FEATURE:
<221> NAME/KEY: source
<222> LOCATION: 1..59
<223> OTHER INFORMATION: /organism="Artificial Sequence"
      /note="PLA probe"
      /mol_type="unassigned DNA"

<400> SEQUENCE: 7
cgcatcgccc ttggactacg actgacgaac cgctttgcct gactgatcgc taaatcgtg      59

<210> SEQ ID NO 8
<211> LENGTH: 61
<212> TYPE: DNA
<213> ORGANISM: Artificial Sequence
<220> FEATURE:
<221> NAME/KEY: source
<222> LOCATION: 1..61
<223> OTHER INFORMATION: /organism="Artificial Sequence"
      /note="PLA probe"
      /mol_type="unassigned DNA"

<400> SEQUENCE: 8
tcgtgtctaa agtccgttac cttgattccc ctaaccctct tgaaaaattc ggcatcggtg      60
a                                                                      61

<210> SEQ ID NO 9
<211> LENGTH: 61
<212> TYPE: DNA
<213> ORGANISM: Artificial Sequence
<220> FEATURE:
<221> NAME/KEY: source
<222> LOCATION: 1..61
<223> OTHER INFORMATION: /organism="Artificial Sequence"
      /note="PLA probe"
      /mol_type="unassigned DNA"

<400> SEQUENCE: 9
tagctaaggc ttagattatt attcttcttc ttcagtgcag gatcacgatt tagatatttt      60
t                                                                      61

<210> SEQ ID NO 10
<211> LENGTH: 64
<212> TYPE: DNA
<213> ORGANISM: Artificial Sequence
<220> FEATURE:
<221> NAME/KEY: source
<222> LOCATION: 1..64
<223> OTHER INFORMATION: /organism="Artificial Sequence"
      /note="PLA probe"
      /mol_type="unassigned DNA"

<400> SEQUENCE: 10 atatttctt tagacacgag tagcatacct tcccttctc tactactcct tcacctcctc        60
cact                                                                   64

<210> SEQ ID NO 11
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /organism="Artificial Sequence"
      /note="primer"
```

-continued

```
        /mol_type="unassigned DNA"

<400> SEQUENCE: 11
catcgccctt ggactacga                                                19

<210> SEQ ID NO 12
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /organism="Artificial Sequence"
        /note="primer"
        /mol_type="unassigned DNA"

<400> SEQUENCE: 12
gggaatcaag gtaacggact ttag                                          24

<210> SEQ ID NO 13
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /organism="Artificial Sequence"
        /note="PLA probe"
        /mol_type="unassigned DNA"

<400> SEQUENCE: 13
tacttagaca cgacacgatt tagttt                                        26

<210> SEQ ID NO 14
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /organism="Artificial Sequence"
        /note="cassette oligonucleotide"
        /mol_type="unassigned DNA"

<400> SEQUENCE: 14
atcctgcact tatattggta tgctac                                        26

<210> SEQ ID NO 15
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /organism="Artificial Sequence"
        /note="probe"
        /mol_type="unassigned DNA"

<400> SEQUENCE: 15
tgacgaaccg ctttgcctga ctga                                          24
```

DETECTION OF SINGLE AND MULTIMODAL ANALYTES

RELATED APPLICATION

The present application claims priority under 35 U.S.C. 119 of U.S. Application No. 61/590,860 filed Jan. 26, 2012.

FIELD OF THE INVENTION

The present invention relates to the field of tools for detection on a molecular level. Specifically, it relates to a novel tool for highly specific detection of analytes with multiple epitopes. It further relates to kits comprising the necessary components for performing such a method.

BACKGROUND OF THE INVENTION

Different forms of proximity ligation assays (PLA) provide tools for detection of analytes with increased sensitivity and specificity compared to many other methods such as ELISA. PLA is a proteome analysis technology where target molecules must be recognized by multiple antibodies, carrying short DNA strands. Upon binding to their targets these DNA strands can be joined by ligation. The method allows amplified detection of the DNA reporter molecules, offering high specificity and sensitivity[12].

WO2007/107743 describes a method named "3PLA", wherein three proximity probes comprising one part specifically binding to an analyte and one part comprising a nucleic acid domain are used to detect analytes.

SUMMARY OF THE INVENTION

The present invention aims to provide a detection method with increased specificity and decreased background noise.

Increased requirement in epitope recognition will result in more specific detection of analytes. This will also, due to decreased level of noise, result in improvement of sensitivity. To overcome the limitation of assay specificity in the methods of the prior art, a new generation of analyte detection method is designed in which an analyte will be detected using four or more recognition events in a homogenous assay format or on a solid support.

It is shown in the examples below that the limit of detection (LOD) is about 150-fold lower for the method according to the invention as compared to a conventional PLA protocol. It also has a dynamic range that extends by two further orders of magnitude as compared to PLA. The assay with its high sensitivity and specificity for biomarkers is promising as a tool in diagnostic and prognostic tests. Potential applications include early diagnosis, monitoring under active surveillance, selection of therapy in localized disease, and monitoring of responses to treatment.

The main aspects of the invention are described in the independent claims. Preferred embodiments are set forth in the dependent claims.

BRIEF DESCRIPTION OF THE DRAWINGS

The Detailed Description will be more fully understood in view of the drawings in which:

FIG. 2A) Comparison of the method according to the invention (circles) and solid-phase PLA (squares) for measuring purified prostasomes. For the method according to the invention the SD of 0.021 and for solid-phase PLA the SD of 0.056 for negative controls were used to calculate the LOD. FIG. 2B) the method according to the invention was used to detect serial dilutions of purified prostasomes, spiked in buffer (squares) or in 10% human plasma (circles). FIG. 2C) The mechanism of the method according to the invention was investigated by omitting each of the four antibodies used in the probe mix in separate reactions, while still adding the corresponding oligonucleotide. The omission of any antibody resulted in reduction of the detection signals to background levels. The Y-axes show the CT average, while the X-axes indicate the concentration of prostasomes. Error bars indicate standard deviations from the mean for triplicate reactions.

FIG. 3A) The analysis of samples from prostate cancer patients (n=20) revealed significantly higher concentrations of prostasomes than those observed in samples from age-matched controls (n=20; p<0.001). FIG. 3B) The higher concentrations of prostasomes in samples from patients were confirmed in a blind-test validation experiment examining the subgroup of 13 patients and 11 age-matched control samples (p<0.001). The results are shown as boxplots in which the dashed lines extend between the minimum and maximum values, boxes extend between the lower and higher quartiles, and the horizontal black bars indicate the medians for the patients and controls, respectively. FIG. 3C) Plasma samples from five prostate cancer patients were pooled, and the level of prostasomes in the supernatant after ultracentrifugation (open bar) was compared with the level in pooled plasma that had not been centrifuged (gray bar). Error bars indicate standard deviations from the mean for triplicate reactions.

DEFINITIONS

Figure 1:
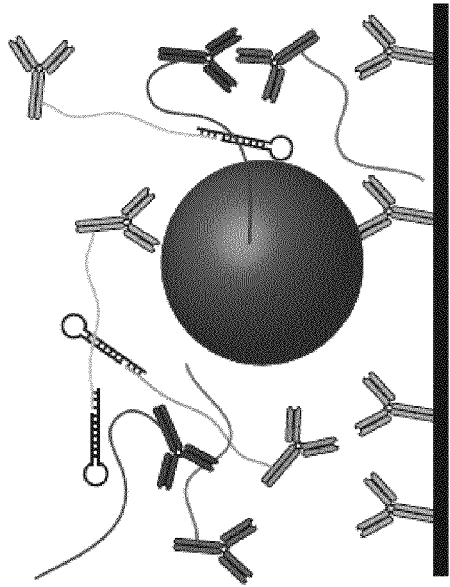
FIGS. 1A-1D shows a schematic outline of the method according to the invention. Target molecules are captured by antibodies immobilized on the walls of a reaction vessel, FIG. 1A, the four PLA probes are added, FIG. 1B, and the probes are allowed to bind different epitopes on the target. Oligonucleotides attached to the antibodies hybridize to each other, FIG. 1C, and guide hybridization of a separate oligonucleotide, FIG. 1D. This oligonucleotide is joined by enzymatic DNA ligation to oligonucleotides attached to two of the antibodies, templated by oligonucleotides on the two other antibodies. Finally, the newly formed DNA template is amplified and quantified by qPCR.
Figure 1:
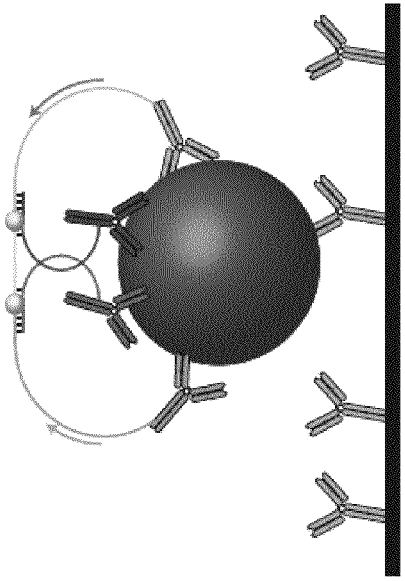
Figure 1:
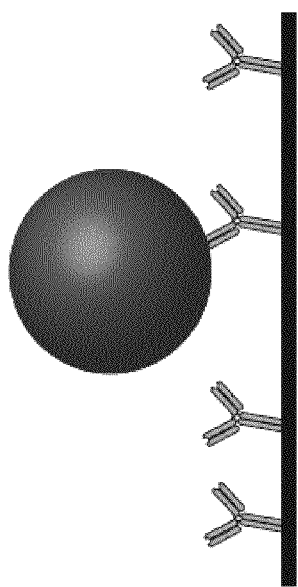
Figure 1:
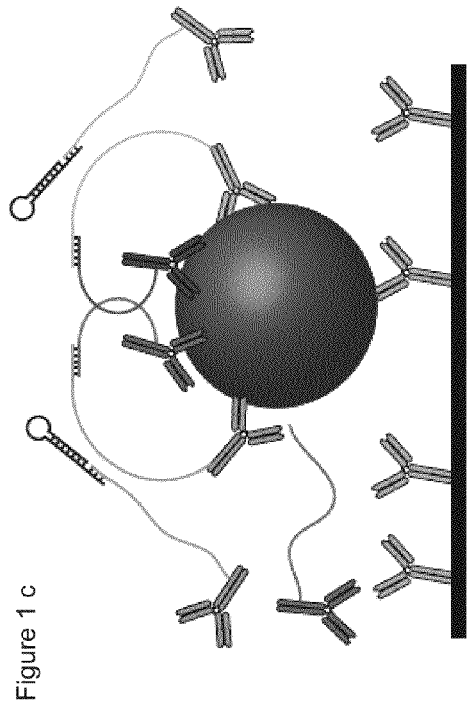

All words and terms used in the present application shall be interpreted to have the meaning usually given to them by the person skilled in the art, unless otherwise indicated. For the sake of clarity, some terms are further explained below.

Proximity Ligation Assay, abbreviated PLA, is the method as described in references 1 and 2.

3PLA is the method as described in WO2007/107743.

RCA is an abbreviation for Rolling Circle Amplification.

Proximity probe is a probe composed of an analyte-binding domain being an affinity binder, and a nucleic acid domain, preferably a single stranded DNA ("ssDNA").

The term "Affinity binder" shall be construed as any molecular entity capable of selectively binding to an analyte of interest. Affinity binders may be polyclonal or monoclonal antibodies, fragments thereof such as F(ab)$_2$, Fab, Fab', Fv, Fc, and Fd fragments, which may be incorporated into single domain antibodies, single-chain antibodies, maxibodies, minibodies, intrabodies, diabodies, triabodies, tetrabodies, v-NAR and bis-scFv[3]. Affinity binders also include synthetic binding molecules such as molecularly imprinted polymers, affibodies or any other affinity binder that can be conjugated to DNA oligonucleotides.

DETAILED DESCRIPTION

The present invention aims to provide a detection method with increased specificity and decreased background noise.

In the method according to the invention affinity binders are equipped with oligonucleotides to form probes. The binders can be conjugated to the ssDNA by different means. One strategy is when the binders are equipped with biotin. In this case the DNA molecules are coupled to streptavidin molecules that have very high affinity to biotin. The binders can also be coupled covalently to the ssDNA molecules using different chemistries. Although polyclonal and monoclonal antibodies are the most common affinity binders but all other affinity binders can be used in the method according to the invention.

Once the proximity probes are prepared, they will be incubated with the target molecule for a given time depending on the kinetics of the binders. To prevent any unspecific interaction of the proximity arms in the absence of the target molecule, two of the proximity arms may be hybridized to blocking oligonucleotides. When the proximity arms are in close proximity to each other the blocking oligonucleotides are, if present, replaced with two other ssDNA arms coupled to two other affinity binders that will subsequently hybridize to a cassette oligonucleotide that in the presence of a ligase will be connected to the two outer proximity arms to form a new amplifiable DNA molecule.

In one embodiment of the invention, the method according to the invention is carried out on a solid support such as magnetic microparticles, inside plastic tubes etc. Here, the target molecule will first be captured using a fifth affinity binder immobilized on the solid support and thereafter the proximity probes will be added and the method according to the invention will be carried out as described above. In the solid-phase embodiment, a wash step can be introduced between each step to remove undesirable components, which might increase the efficiency of the assay.

The method according to the invention can be used for sensitive and specific detection of single proteins that have enough epitopes to be recognized with four different binders in a homogenous manner or five binders in a heterogonous format. The method can also be used for detection and analysis of interaction of two or more target molecules, for instance proteins, DNA and RNA or other polymers. It can also be used for detection and analyses of pathogens—such as bacteria, viruses and parasites—detection of cells, for instance tumor cells in circulation, and it can also be used for detection of aggregated proteins such as A-beta oligomers, alfa-synuclein, amyloidosis etc. In addition, the method according to the invention has been shown to be a powerful tool for specific detection of organelles such as exosomes.

A schematic outline of the solid-phase embodiment of the invention is illustrated in FIG. 1; a) The target molecules, for instance, prostasomes, are captured by immobilized antibodies, followed by the addition of (b) four oligonucleotide-conjugated antibodies against four different epitopes or four different proteins present on the target molecules. (c) Blocking oligonucleotides are replaced with the PLA probe arms that are in close proximity, allowing the hybridization of a cassette oligonucleotide to the accessory PLA probe arms allowing the enzymatic ligation (d) of the cassette oligonucleotide to the adjacent oligonucleotides. The ligation of the blocking oligonucleotides to unbound probes, block the non-specific ligations between those oligonucleotides. The newly formed ligation products are amplified using two primers designed to recognize two different proximity probes.

By using the extremely sensitive and specific method according to the invention we demonstrate here (Example 1) for the first time that prostasomes can be detected at elevated levels in blood plasma from prostate cancer patients.

The test according to the invention, which depends on simultaneous recognition of targets by four different antibodies recognizing five different epitopes, exhibits improved sensitivity and specificity for prostasomes compared to solid-phase PLA where three recognition events are involved. This improvement may be explained in part by the lower risk of target-independent proximity of all the binders and thus non-specific background, but the method according to the invention also provides particular advantages for detection of multiprotein complexes as diagnostic targets. To our knowledge, this is the first assay that depends on simultaneous binding to as much as five different epitopes for detection. The present invention expands the scope for biomarker diagnostics by providing the possibility to measure in body fluids such as blood plasma previously inaccessible classes of markers, such as complexes of interacting proteins, aggregates and multiprotein particles, e.g. microvesicles. The available technologies for sensitive protein detection typically use pairs of affinity reagents in a sandwich configuration. This is true for the popular sandwich ELISA and for more recent highly sensitive techniques such as the bio-barcode assays and homogeneous PLA.

The specificity of the method according to the invention is illustrated by the lack of signals in the supernatant of ultracentrifuged blood plasma samples from prostate cancer patients, and by the failure to detect prostasomes in plasma from prepubertal boys. This was in agreement with previous investigations, demonstrating the androgen dependence of prostasome production and secretion[4,5] (42, 49). In contrast to measurements of PSA, the prostasome test could distinguish prostate cancers with low and high Gleason scores.

The assay with its high sensitivity and specificity for prostasomes in blood samples is promising as a diagnostic and prognostic test for prostate cancer. Potential applications include early diagnosis, monitoring under active surveillance, selection of therapy in localized disease, and monitoring of responses to treatment.

EXAMPLES

Example 1

Prostasome Detection

The method according to the invention was used to detect prostasomes in blood plasma from prostate cancer patients and controls. It was successfully established that prostasomes are present in blood plasma, and we observed increased levels in samples from prostate cancer patients.

A wide variety of cell types are able to release microvesicles of endocytic origin to the extracellular compartment. The first cellular system to be explored in this regard was the prostate acinar cells. Ronquist et al. showed more than 30 years ago that human prostatic fluid and seminal plasma contain membrane-surrounded, nanometer-sized microvesicles Subsequent studies revealed that these extracellular organelles, now denoted prostasomes, had their intracellular correspondence to similar organelles inside another larger organelle, a so-called storage vesicle, equivalent to multivesicular bodies or late endosomes. Accordingly, the release of prostasomes to the extracellular compartment is the result of a fusion between the membrane surrounding the storage vesicle and the plasma membrane of the secretory cell of the prostate gland (exocytosis). The prostasomal membrane displays extraordinary properties with an unusually high content of the phospholipid sphingomyelin and a high cholesterol/phospholipid ratio rendering the membrane highly ordered and solid, as reflected by resistance to detergents.

Prostasomes contain several protein molecules. Proteins present on the surface of prostasomes include aminopeptidase N (CD13) and tissue factor (CD142) a cell membrane-associated glycoprotein that serves as a receptor and essential cofactor for factors VII and VIIa of the coagulation cascade.

Prostasomes seem to act as intercellular messengers between prostate secretory cells and sperm cells, transferring molecules propitious for fertilization by influencing e.g. sperm motility, and exerting antibacterial, complement inhibitory, antioxidant and immunosuppressive activities.

Also neoplastic prostate cells have the capacity to synthesize and export prostasomes, even poorly differentiated prostate cancer metastases, but the altered tissue architecture in malignancy facilitates the release of prostasomes to the interstitial space.

Materials and Methods

Plasma Samples from Patients and Controls

Blood plasma was obtained from two groups of prostate cancer patients and compared to age-matched controls. A first group included samples from 20 patients (52-69 years old) having PSA levels between 94 µg/l to 2706 µg/l and 20 age-matched controls with PSA levels below 2.5 µg/l. In a second group, we investigated samples from 59 patients (53-73 years old) having PSA levels between 1.1 µg/l to 39.1 µg/l. These were compared to 20 age-matched controls (53-75 years old) with benign results from transrectal ultrasound guided biopsy and PSA levels between 1.7 to 14.8 µg/l. Thirteen patients (PSA values, 4.3-22.2 µg/l) and 11 controls (PSA values, 2.7-14.8 µg/l) were recruited from the second group to constitute a subgroup for a blinded validation experiment, see Results. All analyses of the first group were approved by the ethical committee of Uppsala University. The samples of the second group were collected under a protocol approved by the Internal Review Board of the University of Münster in accordance with practices and ethical standards of the Committee on Ethical Issues of the university and the Declaration of Helsinki, including informed consent by the patients.

Reagents

Antibodies

Monoclonal antibodies mAb78 and mAb8H10, directed against seminal prostasomes, were produced in mice by intrasplenic immunization and the antibodies were biotinylated as described[6,7,8]. Anti-CD13 monoclonal antibody was from AbD Serotec (Kidlington, UK). Biotinylated, polyclonal anti-human coagulation factor III/tissue factor antibodies were purchased from R&D Systems (cat. #BAF2339).

Prostasome Preparation

Fresh semen samples were obtained from normospermic men according to the WHO laboratory manual, during evaluation for in vitro fertilization. Semen samples were centrifuged for 20 min at 1,000 g at 21° C. to pellet spermatozoa and any other cells from the seminal plasma.

Seminal prostasomes were prepared from pooled seminal plasmas by procedures including differential centrifugation, preparative ultracentrifugation, and separation by gel chromatography as previously described[8]. All preparatory procedures were carried out at 0-4° C. if not otherwise stated.

Preparation of Probes

Sequences for all oligonucleotides are shown in Table 1. All oligonucleotide-streptavidin conjugates used to prepare PLA probes for the method according to the invention and solid-phase PLA tests were combined with free streptavidin and briefly heated to obtain streptavidin tetramers containing reduced number of oligonucleotides as described[9]. 100 nM oligonucleotide-streptavidin conjugates were incubated with 100 nM biotinylated antibodies in phosphate-buffered saline (1×PBS) for 1 h at 21° C. The conjugated probes were diluted in buffer (10 mM Tris-HCl pH 7.5, 10 mM MgCl2, 0.025% Tween 20 (Sigma-Aldrich), 1 mM D-biotin (Invitrogen), 1% BSA and 100 mM NaCl), incubated for 20 min at 21° C., and stored at 4° C. for up to two months. The oligonucleotides SLC1 and SLC2 were conjugated to mAb78 and mAb8H10, respectively, and the oligonucleotides Acc1 and Acc2 were conjugated to polyclonal anti-human coagulation factor III/tissue factor, respectively.

The pair of antibodies used to prepare PLA probes for PLA according to a previously published protocol[10] were mAb78 and mAb8H10, and the four PLA probes in the method according to the invention used mAb78, mAb8H10 and two aliquots of polyclonal anti-tissue factor antibodies. In the method according to the invention the oligonucleotides attached to two of the PLA probes were designed to hybridize to hairpin-loop structured blocking oligonucleotides to prevent hybridization to the other PLA probes in the absence of target binding. Once bound in proximity these hybrids are replaced by hybrids between oligonucleotides on different antibodies. After washes a short bridging oligonucleotide is added to join the oligonucleotides on two PLA probes via two enzymatic ligation reactions. Oligonucleotides on PLA probes having failed to bind in proximity become ligated to the blocking oligonucleotides, thus preventing nonspecific generation of amplifiable DNA strands.

Detection of Prostasomes by PLA and the Method According to the Invention

Prostasomes were detected by PLA essentially as described[10] or as adapted for the method according to the invention. Briefly, capture antibodies were immobilized in reaction tubes (AJ Roboscreen GmbH, Germany) using 50 µl of 1 ng/µl anti-CD13 in coating buffer (0.05 M sodium bicarbonate, 0.05 M sodium carbonate, 0.015 M sodium azide, pH 9.6) at 4° C. over night. Excess antibodies were removed by three washes in 1×TBS and 0.01% (v/v) Tween 20.

Fifty µl purified prostasomes or blood plasma samples from patients or controls, diluted tenfold in buffer, were added to the tubes and incubated for 2h at 37° C., followed by three washes as described above. Next, 50 µl of 500 pM PLA probe mixtures were added, and the tubes were incubated at 37° C. for 2 h and unreacted probes were removed as above. Thereafter, 50 µl ligation/amplification mix was added, containing 1× PCR buffer (Invitrogen), 2.5 mM MgCl2 (Invitrogen), 0.2 µM of each Biofwd and Biorev primer, 0.4 µM TAQMAN® probe, 0.08 mM ATP, 0.2 mM of each deoxynucleoside triphosphate (containing dUTP), 1.5 unit Platinum Taq DNA polymerase (Invitrogen), 0.5 Weiss units of T4 DNA ligase (Fermentas), 0.1 unit uracil-DNA glycosylase (Fermentas) and 40 nM cassette oligonucleotide for the method according to the invention and 200 nM connector oligonucleotide for PLA. The reactions were incubated for 5 min at 21° C. and qPCR was then performed in an MX-3000™ or MX 3005™ real time PCR instrument (Stratagene), with an initial incubation for 2 min at 95° C., followed by 45 cycles of 95° C. for 15 s and 60° C. for 1 min. The results were presented as threshold cycle (CT) values. For clinical samples the CT values were converted into mass quantities by using data from a prostasome standard curve run in same experiment and prostasomes were expressed as ng/ml blood plasma.

Data Analysis

The qPCR data were analyzed with MXPRO™ real time PCR software (Stratagene), and the recorded CT values were exported and further analyzed using the R statistics software package. Logistic regression models were calculated using the drc package in R. The statistical significance of the difference in levels of prostasomes between patient and control groups as determined by the method according to the invention was calculated using a two-sample Wilcoxon rank sum test in R.

Lower limits of detection (LOD) were determined as the concentrations that resulted in a signal two standard deviations (SD) above the mean background levels.

Results

Detection of Prostasomes Using the Method According to the Invention and PLA

To measure prostasomes in blood plasma as potential markers for prostate cancer we established an assay where detection depends on simultaneous recognition of five different protein epitopes on the surface of the prostasomes using four different mono- and polyclonal antibodies. Prostasomes were first captured by a monoclonal antibody against CD13, immobilized on the surfaces of reaction tubes. Next, four oligonucleotide-conjugated antibodies (two monoclonals and one polyclonal (×2)) directed against different epitopes on the surface of the prostasomes were added. Two aliquots of a polyclonal antibody directed against tissue factor had been modified with two different oligonucleotides, and two prostasome-specific monoclonal antibodies called mAb78 and mAb8H10 each carried its own oligonucleotide. After washes, all four oligonucleotides contributed to the creation of an amplifiable DNA strand via two enzymatic ligation reactions. Finally, the amount of target dependent ligation products was measured by qPCR (FIG. 1).

Figures 2A, 2B, 2C:
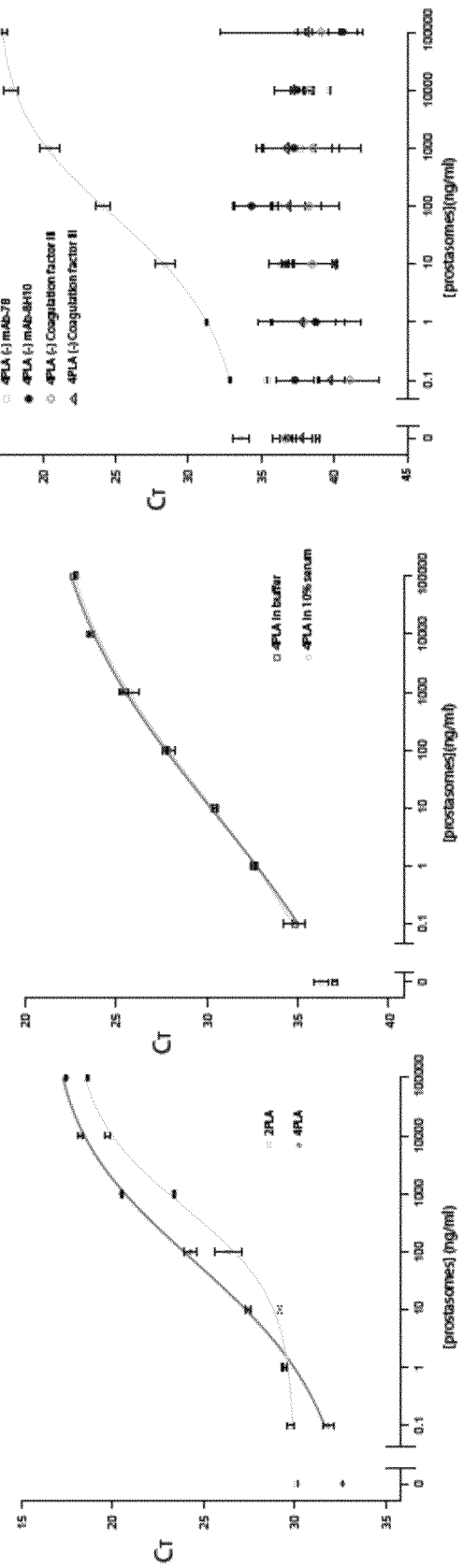
FIGS. 2A-2C show detection of prostasomes using the method according to the invention and PLA.

Prostasomes were detected with a LOD of 0.032 ng/ml. Using a more conventional PLA protocol involving one capture antibody but only two PLA probes the LOD was 4.83 ng/ml (FIG. 2A). Thus, the method according to the invention exhibited around 150-fold lower LOD and it had a dynamic range that extended by two further orders of magnitude compared to PLA. Similar sensitivities and dynamic ranges were observed whether prostasomes were detected by the method according to the invention in either 10% human blood plasma or in buffer (FIG. 2B).

To ascertain that the detection reaction in fact depends on binding by all four PLA probes we replaced one probe at a time with the corresponding concentration of the free oligonucleotide, normally attached to that particular antibody. FIG. 2C shows that omission of any of the antibodies resulted in background level signals, confirming that the assay measures complexes capable of being recognized by all antibodies.

Detection of prostasomes in plasma samples from prostate cancer patients

Figure 3A:
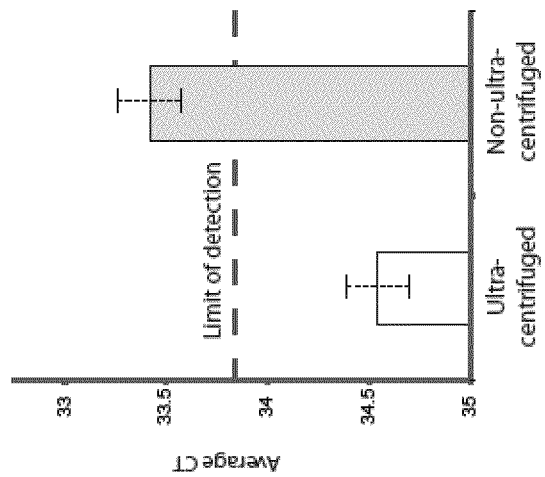
FIGS. 3A-3C show levels of prostasomes in plasma samples from patients and controls as measured with the method according to the invention.
Figure 3B:
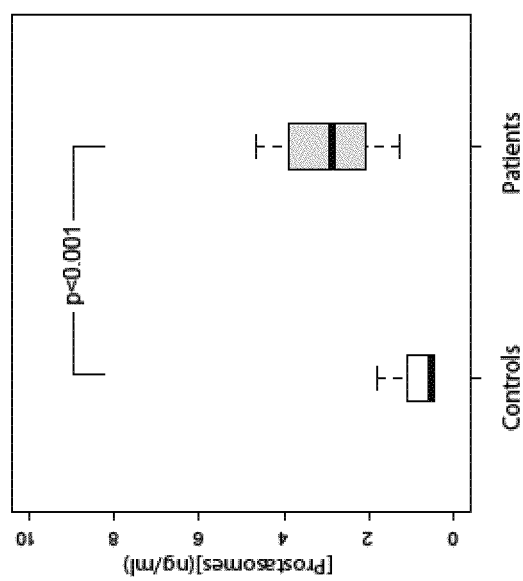

We investigated levels of prostasomes in blood plasma samples from patients with prostate cancer and controls using the method according to the invention. Significantly increased levels of prostasomes were observed in blood plasma from 20 prostate cancer patients (median, 7.7 ng/ml; range 1.1-34.9; 95% confidence interval (CI)) compared to 20 age-matched controls (median 1.1; range<1.1-12.4; 95% CI); p<0.001; FIG. 3A). In a separate, blinded validation experiment prostasome levels again were elevated in another constellation (the subgroup) of 13 patients (median, 2.9 ng/ml; range 1.3-4.6 ng/ml; 95% CI) compared to 11 age-matched controls (median, 0.5 ng/ml; range 0.5-1.8 ng/ml; 95% CI; p<0.001; FIG. 3B). No prostasomes were detected in blood plasma samples from 12 prepubertal boys at ages where the prostate gland is known not to produce and secrete prostasomes[11] (data not shown).

Figure 3C:
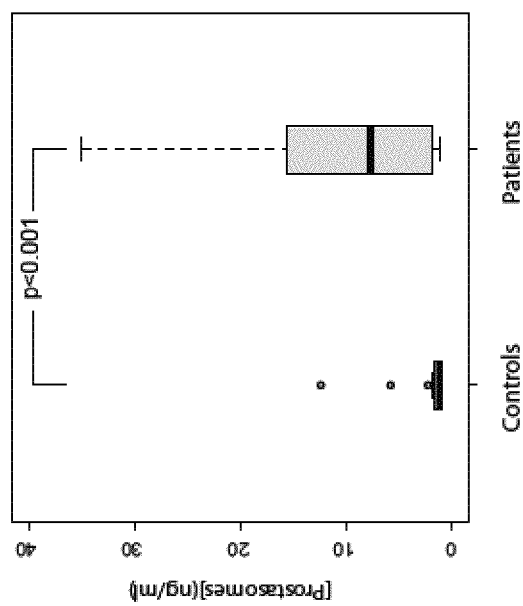

In order to further establish that the method according to the invention indeed detects prostasomes rather than individual proteins, a pooled plasma sample from five prostate cancer patients with plasma PSA values between 10 and 120 µg/l was ultracentrifuged at 200,000×g for 2 h to ascertain that the prostasomes were quantitatively pelleted. Prostasomes were not detected in supernatant of plasma samples subjected to ultracentrifugation, while they were readily detected by the method according to the invention in the sample not subjected to ultracentrifugation (FIG. 3C).

Figure 4:
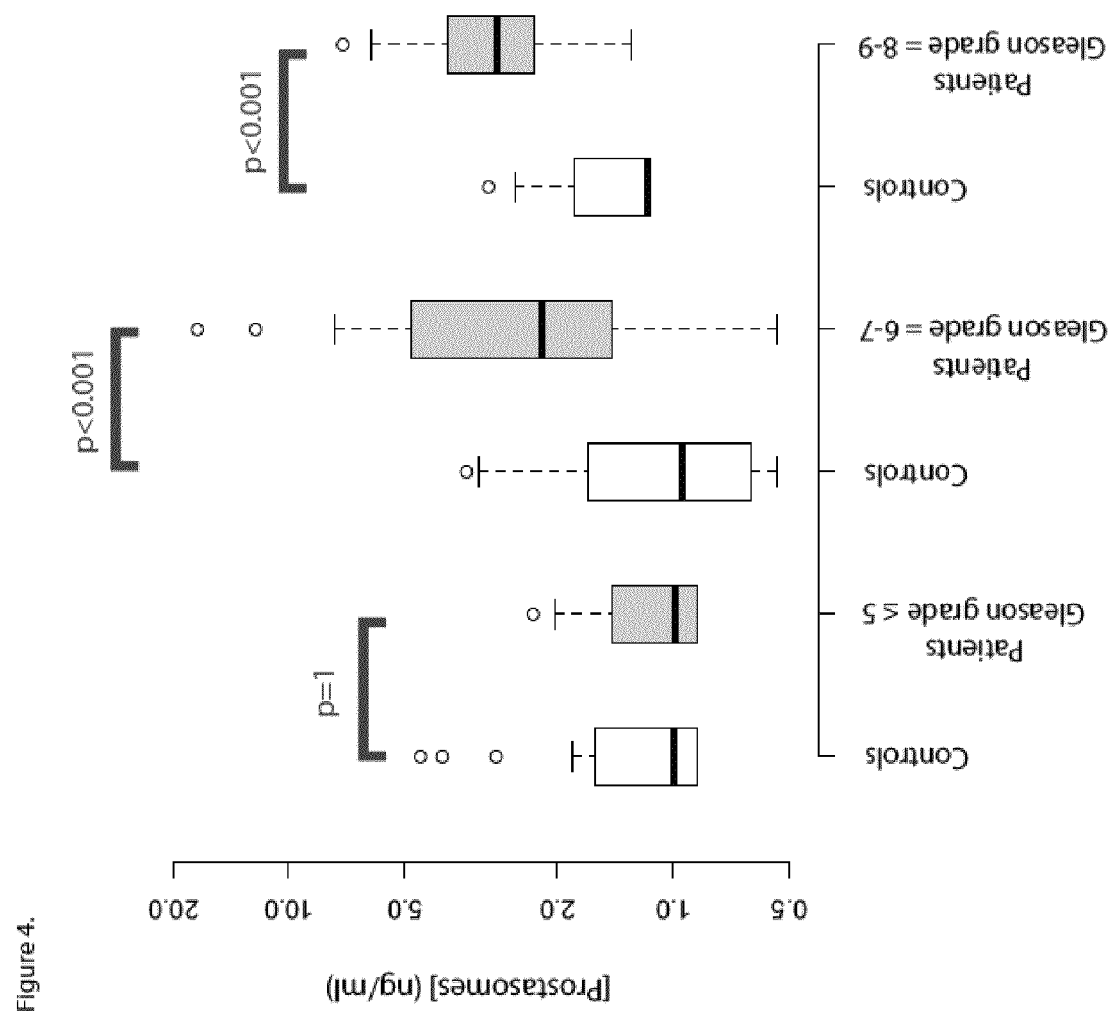
FIG. 4: Plasma levels of prostasomes in samples from prostate cancer patients grouped according to histological Gleason scores. The patients were classified in three groups. Each patient group was analyzed in a separate batch together with the control group. The levels of prostasomes in plasma samples from patients with Gleason score 6-7 and 8-9 were both significantly higher than those with a Gleason score of 5 and of controls with p-values of 0.001. The levels of prostasomes in samples from patients with Gleason score 5 were similar to those in samples from controls (p=1).

Finally, we investigated the relation between blood plasma prostasome levels before therapy and histological evidence of aggressiveness of prostate cancer in a cohort of 59 patients whose tumors were histologically classified after radical prostatectomy as having Gleason scores from 5 to 9. A higher Gleason score means that the tumor deviates more from normal prostate glandular tissue by being less well differentiated. The patients were divided in three groups with a low Gleason score of 5 (n=19), medium scores of 6-7 (n=20), and high scores of 8-9 (n=20). Blood plasma levels of prostasomes were measured by the method according to the invention for each of the groups and compared to levels for the same group of control individuals. Prostate cancer patients with a Gleason score of 5 had prostasome levels similar to those of controls (median, 1.0 ng/ml; range 0.9-2.3 ng/ml for patient samples vs. median 1.0 ng/ml; range 0.9-4.5 ng/ml for control samples; P=1), while the levels in patient groups with Gleason scores of 6-7 or 8-9 (medians, 2.2 and 2.9 ng/ml; range 0.5-17.3 and 0.3-7.2 ng/ml, respectively) were both significantly elevated compared to their respective controls (medians, 0.9 and 1.2 ng/ml; range 0.5-3.5 and 1.2-3.0; p<0.001 for both groups; FIG. 4). The medians for prostasome levels in patient samples were between 2.5- and 7-fold higher than the medians for background prostasome level in control samples.

Figure 5A:
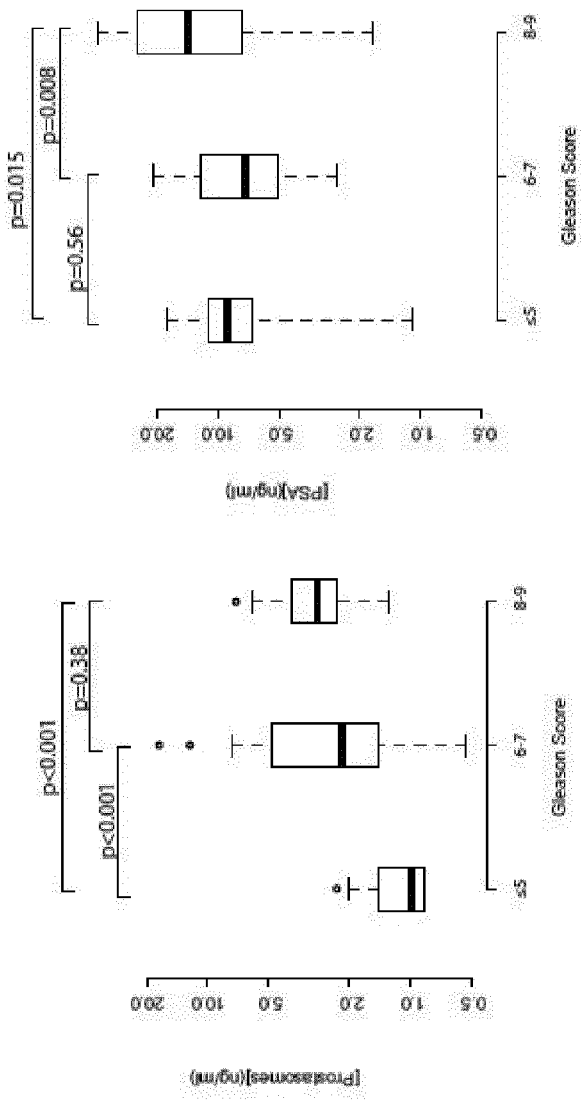
FIG. 5A shows boxplots showing differences in levels of prostasomes and PSA, respectively, in patient groups with different Gleason scores. The p-values were calculated using a two-sample Wilcoxon rank sum test.
Figure 5B:
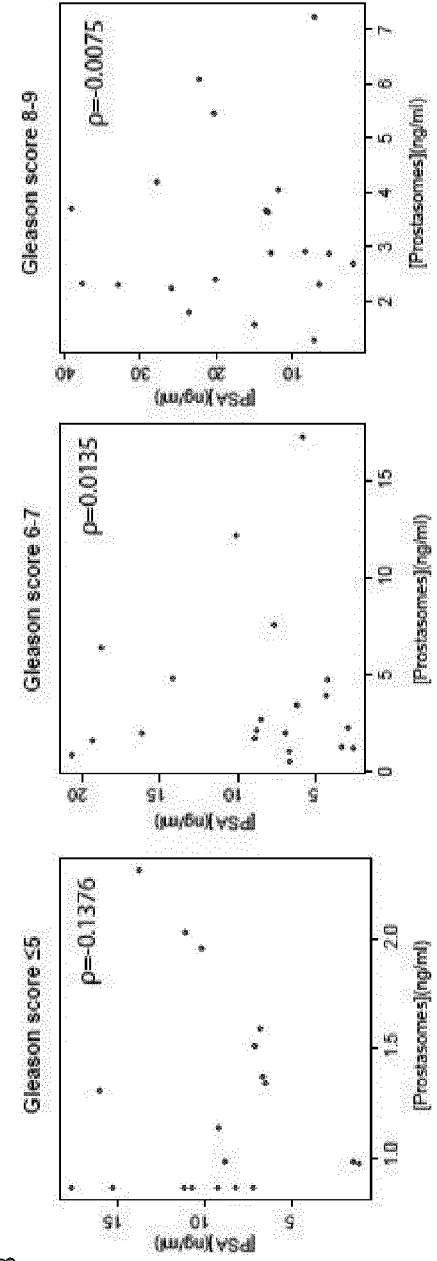
FIG. 5B) shows scatter plots illustrating the correlation between plasma prostasome and PSA levels for patients divided in three groups with Gleason score of 5 (n=19), scores of 6-7 (n=20) and scores of 8-9 (n=20). Rho-values (ρ) are Spearman's rank correlation coefficients, measuring the statistical dependence of PSA and prostasome levels upon Gleason scores.

The PSA test did not distinguish patients with Gleason scores of 6-7 from those with score of 5 (p=0.56), but they could only distinguish the patients with Gleason scores of 6-7 from those with Gleason scores of 8-9 (p<0.008; FIG. 5A). The prostasome and PSA levels did not correlate in any of the three patient groups (FIG. 5B).

Example 2

Figure 6:
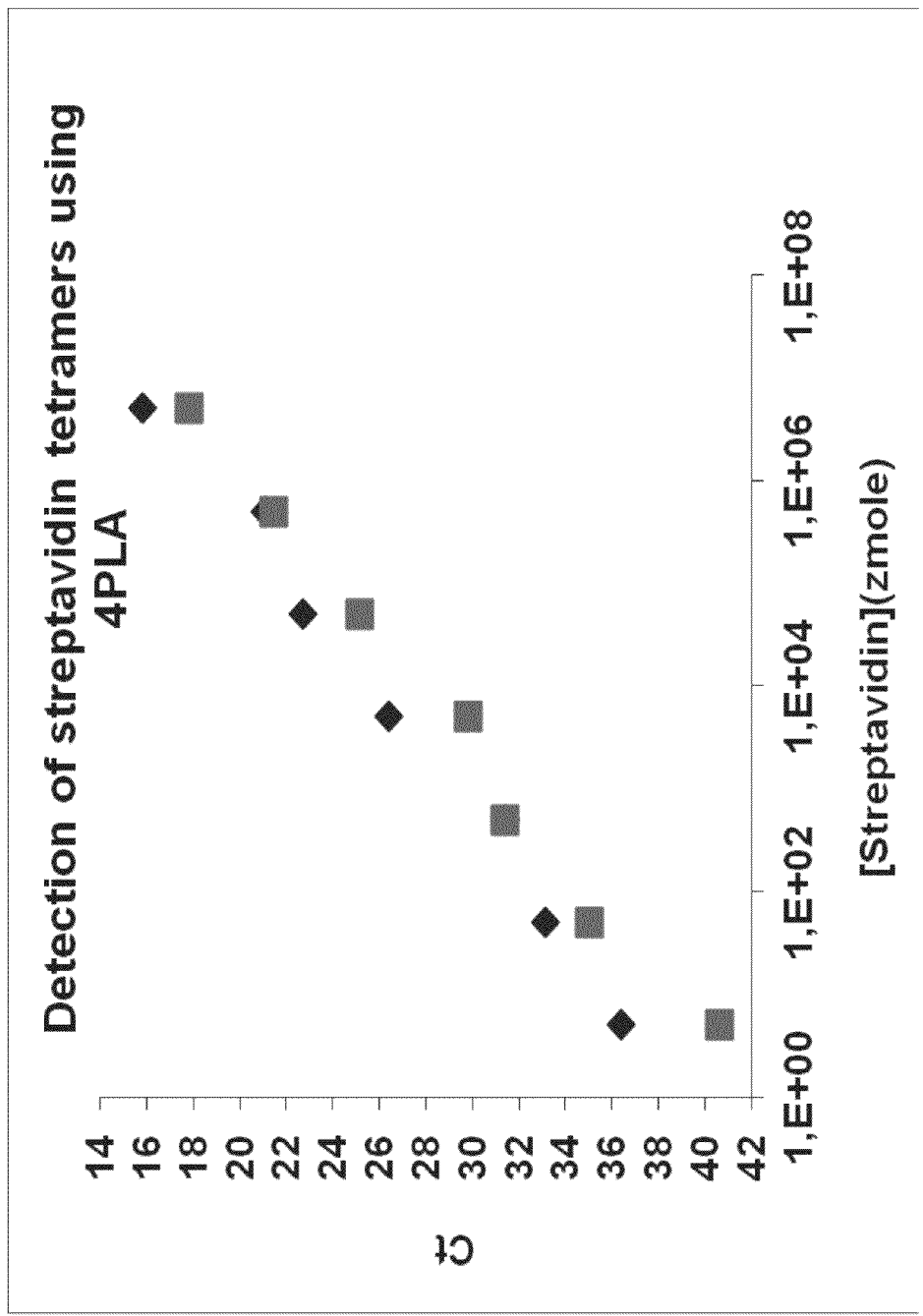
FIG. 6 shows detection of tetramer strepavidin using a homogenous version of the method according to the invention. The four proximity probes were coupled to biotin and were used to detect streptavidin Diamonds and squares demonstrating 2 different probe concentrations

Detection of tetramer strepavidin using a homogenous version of the method according to the invention. Streptavidin tetramers (5 μl) at variant concentrations were incubated with probe mix containing four different biotinylated oligonucleotides for one hour. 40 μl ligation/PCR mix (containing: 1×PCR buffer, 2.5 mM $MgCl_2$, 0.2 μM of each forward and reverse primers, 0.4 μM TaqMan probe, 0.08 mM ATP, 100 nM cassette oligonucleotide, 0.2 mM dNTPs, 1.5 units Platinum Taq polymerase, 0.5 units T4 DNA ligase) was added and real-time PCR was performed. Diamonds and squares demonstrating 200 and 500 pM probe concentration, respectively. X-axis indicates streptavidin concentration while Y-axis indicates Ct average (FIG. 6).

Example 3

Figure 7:
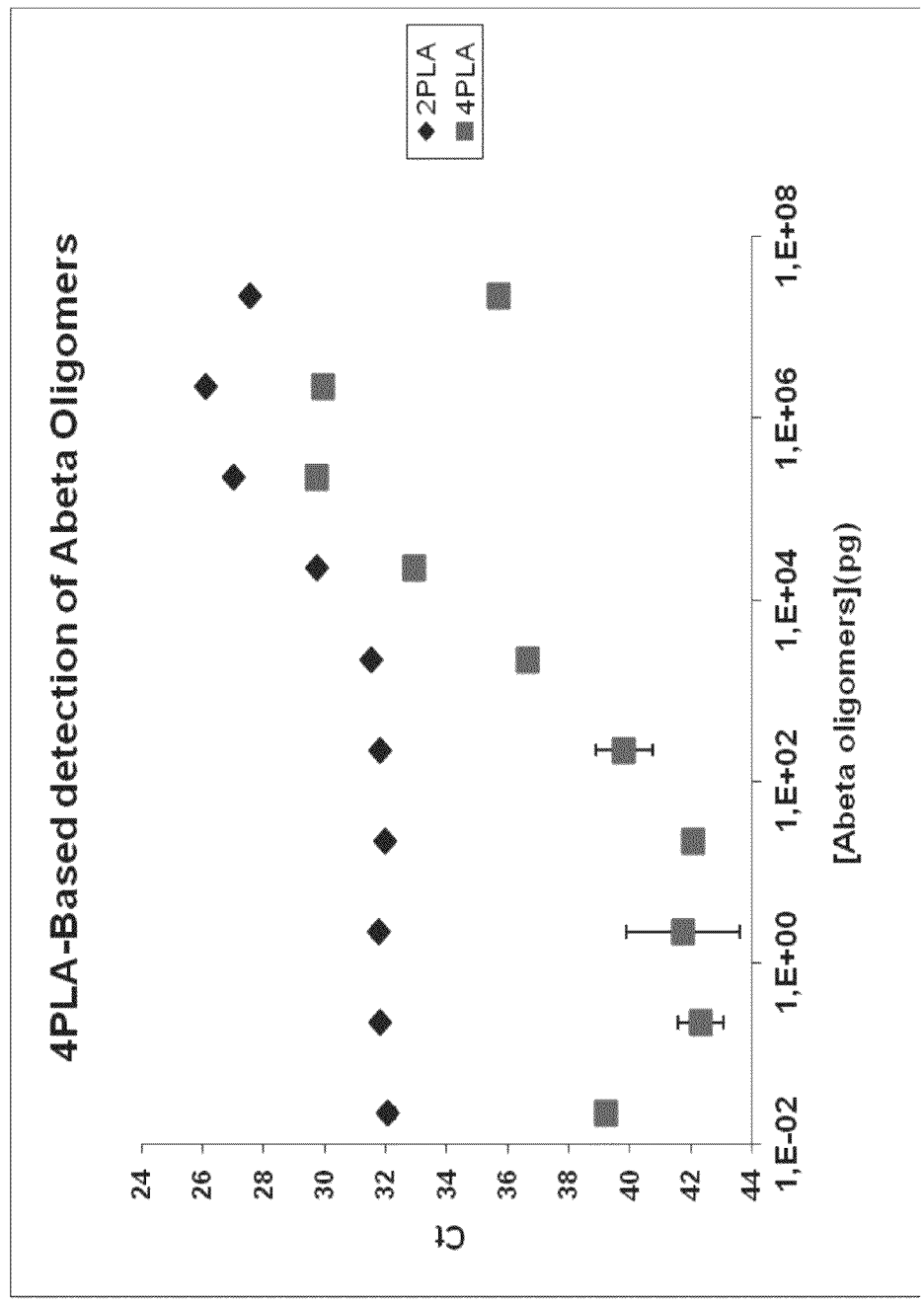
FIG. 7 shows detection of A-beta oligomers using the method according to the invention versus conventional PLA. A single monoclonal antibody conjugated to four different DNA oligonucleotides that were used for specific detection of A-beta oligomers.

Detection of A-beta oligomers using the method according to the invention versus conventional PLA. Five μl Probe mix, containing four different oligonucleotides conjugated to a single monoclonal antibody, were incubated with soluble aggregated Aβ oligomers for one hour. After incubation, 40 μl PCR/ligation mix was added and real-time PCR was performed. Squares indicate detection of Aβ oligomers using the method according to the invention and diamonds indicate detection of Aβ oligomers using conventional PLA. X-axis indicates concentration of Aβ oligomers while Y-axis indicates Ct average (FIG. 7).

Example 4

Figure 8:
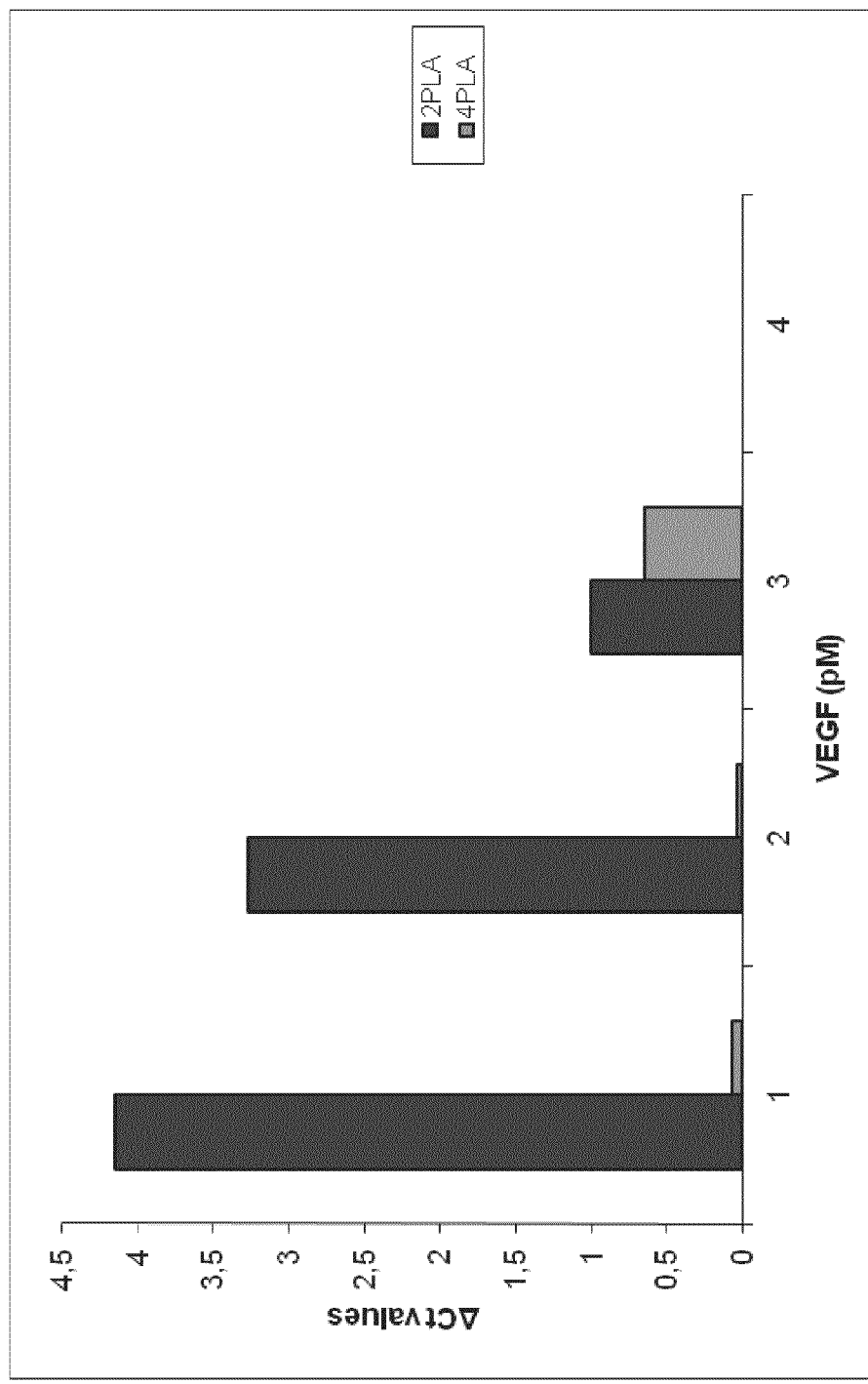
FIG. 8 shows the method according to the invention demonstrated increased specificity. To demonstrate the increased specificity, human VEGF was captured using an anti-human-VEGF antibody immobilized on a solid support and after washes the antigen was detected with probes containing oligonucleotides conjugated to either anti-VEGF antibodies or conjugated to an irrelevant antibody (anti-PDGF).
Figure 9:
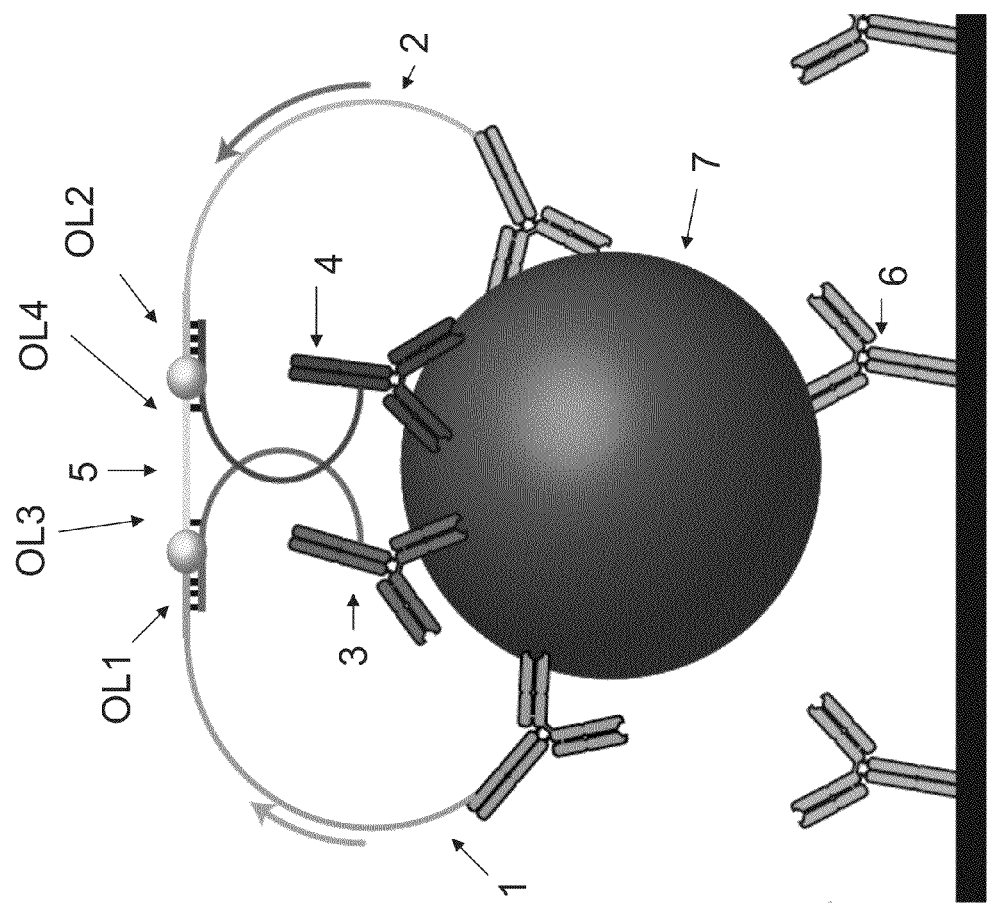
FIG. 9 shows a general illustration of the invention according to claim 2, showing first to fourth proximity probes (1-4), a cassette oligonucleotide (5), an analyte-binding moiety bound to a solid support (6), first to fourth overlapping regions (OL1-OL4)

Increased specificity for the method according to the invention. To demonstrate the increased specificity, human VEGF was captured using an anti-human-VEGF antibody immobilized on a solid support and after washes the antigen was detected with probes containing oligonucleotides conjugated to either anti-VEGF antibodies or conjugated to an irrelevant antibody (anti-PDGF). While conventional PLA showed a signal-to-noise ratio of up to 4 Ct the signal-to-noise ratio obtained for the method according to the invention were close to background (FIG. 8).

The present invention is not limited to the above-described preferred embodiments. Various alternatives, modifications and equivalents may be used. Therefore, the above embodiments should not be taken as limiting the scope of the invention, which is defined by the appending claims.

TABLE 1

Sequences of oligonucleotides used in Example 1

| Name | Sequence | Modification | Company |
| --- | --- | --- | --- |
| SLC1 | CGCATCGCCCTTGGACTACGACTGACGAACCGCTTTGCCTGACTGATCGCTAAATCGTG (SEQ ID: 1) | 5'-strepavidin | Soluiink |
| SLC2 | TCGTGTCTAAAGTCCGTTACCTTGATTCCCCTAACCCTCTTGAAAAATTCGGCATCGGTGA (SEQ ID: 2) | 5'-phosphate, 3'-strepavidin | Soluiink |
| Acc 1 | TAGCTAAGGCTTAGATTATTATTCTTCTTCTTCAGTGCAGGATCACGATTTAGATATTTTT (SEQ ID: 3) | 5' strepavidin | Soluiink |
| Acc 2 | ATATTTTCTTTAGACACGAGTAGCATACCTTCCCCTTCTCTACTACTCCTTCACCTCCTCCACT (SEQ ID: 4) | 3'-strepavidin | Soluiink |
| Block1 | CTG CATGACGCTAGCTGACATTTTTTGTCAGCTAGCGTCATGCAGCACGAAAA (SEQ ID: 5) | 5'-phosphate | Integrated DNA Technology |
| Block 2 | TTTCACGATACGTAGACTTCGGATTCAGTTTTTTACTGAATCCGAAGTCTACGTA (SEQ ID: 6) | | Integrated DNA Technology |
| Bv free 3' | CGCATCGCCCTTGGACTACGACTGACGAACCGCTTTGCCTGACTGATCGCTAAATCGTG (SEQ ID: 7) | 5'-biotin | Integrated DNA Technology |
| Bv free 5' | TCGTGTCTAAAGTCCGTTACCTTGATTCCCCTAACCCTCTTGAAAAATTCGGCATCGGTGA (SEQ ID: 8) | 5'-posphate, 3'-biotin | Integrated DNA Technology |
| Bvacc 1 | TAGCTAAGG CTTAGATTATTATTCTTCTTCTTCAGTGCAGGATCACGATTTAGATATTTTT (SEQ ID: 9) | 5'-biotin | Soluiink |
| Bvacc 2 | ATATTTTCTTTAGACACGAGTAGCATACCTTCCCCTTCTCTACTACTCCTTCACCTCCTCCACT (SEQ ID: 10) | 3'-biotin | Soluiink |

TABLE 1-continued

Sequences of oligonucleotides used in Example 1

| Name | Sequence | Modification | Company |
|---|---|---|---|
| biofwd | CATCGCCCTTGGACTACGA (SEQ ID: 11) | | Integrated DNA Technology |
| biorev | GGGAATCAAGGTAACGGACTTTAG (SEQ ID: 12) | | Integrated DNA Technology |
| biosplint | TACTTAGACACGACACGATTTAGTTT (SEQ ID: 13) | | Biomer |
| 4PLA Cassette | ATCCTGCACTTATATTGGTATGCTAC (SEQ ID: 14) | 5'-phosphate | Integrated DNA Technology |
| TaqMan® MGB probe | TGACGAACCGCTTTGCCTGACTGA (SEQ ID: 15) | 5'-FAM, 3'-MGBNFQ | Applied Biosystems |

References

1. Fredriksson S, Gullberg M, Jarvius J, et al. Protein detection using proximity-dependent DNA ligation assays. Nat Biotechnol 2002; 20:473-7
2. Gullberg M, Gustafsdottir S M, Schallmeiner E, et al. Cytokine detection by antibody-based proximity ligation. Proc Natl Acad Sci USA 2004; 101:8420-4
3. Hollinger and Hudson, 2005, Nature Biotechnology, 23, 9, 1126-1136
4. Renneberg H, Wennemuth G, Konrad L, Aumuller G. Immunohistochemistry of a prostate membrane specific protein during development and maturation of the human prostate. J Anat 1997; 190 (Pt 3):343-9.
5. Ronquist G, Stegmayr B. Prostatic origin of fucosyl transferase in human seminal plasma—a study on healthy controls and on men with infertility or with prostatic cancer. Urol Res 1984; 12:243-7
6. Nilsson B O, Jin M, Einarsson B, Persson B E, Ronquist G. Monoclonal antibodies against human prostasomes. Prostate 1998; 35:178-84
7. Nilsson B O, Svalander P C, Larsson A Immunization of mice and rabbits by intrasplenic deposition of nanogram quantities of protein attached to Sepharose beads or nitrocellulose paper strips. J Immunol Methods 1987; 99:67-75.
8. Carlsson L, Nilsson O, Larsson A, Stridsberg M, Sahlen G, Ronquist G. Characteristics of human prostasomes isolated from three different sources. Prostate 2003; 54:322-30.
9. Darmanis S, Yuan Nong R, Hammond M, et al. Sensitive plasma protein analysis by microparticle-based proximity ligation assays. Mol Cell Proteomics 2009.
10. Ericsson O, Jarvius J, Schallmeiner E, et al. A dual-tag microarray platform for high-performance nucleic acid and protein analyses. Nucleic Acids Res 2008; 36:e45.
11. Renneberg H, Wennemuth G, Konrad L, Aumuller G Immunohistochemistry of a prostate membrane specific protein during development and maturation of the human prostate. J Anat 1997; 190 (Pt 3):343-9

The invention claimed is:

1. A method for detecting an analyte in a sample, wherein the analyte can simultaneously bind four analyte-binding domains, comprising:

(a) contacting said sample with at least one set comprising a cassette oligonucleotide and first, second, third and fourth proximity probes, which probes each comprise an analyte-binding domain and a nucleic acid domain, wherein the respective analyte-binding domains simultaneously bind to the analyte;

wherein the nucleic acid domains of said first and said third proximity probes include respective first overlapping regions which are complementary and can hybridize and the nucleic acid domains of said second and said fourth proximity probes include respective second overlapping regions which are complementary and can hybridize; and wherein said cassette oligonucleotide and the nucleic acid domain of said third proximity probe include respective third overlapping regions which are complementary and can hybridize, and said cassette oligonucleotide and the nucleic acid domain of said fourth proximity probe include respective fourth overlapping regions which are complementary and can hybridize;

(b) hybridising the respective overlapping regions of said proximity probes and said cassette oligonucleotide; and (c) detecting the analyte in the sample based on detecting a hybridization product of step (b).

2. A method according to claim 1, wherein said sample is further contacted with an analyte-binding moiety bound to a solid support and the analyte binds to the solid support via the analyte binding moiety.

3. A method according to claim 2, wherein analyte-binding moiety is an antibody which binds to a different epitope of the analyte than the analyte-binding domains.

4. A method according to claim 1, wherein said first and second overlapping regions on the first and second proximity probes are respectively located at the ends of the nucleic acid domains of said first and second proximity probes.

5. A method according to claim 1, further comprising ligating the ends of the nucleic acid domains of said first and second proximity probes to the ends of said cassette oligonucleotide.

6. A method according to claim 1, wherein said overlapping regions independently are 5-20 basepairs in length.

7. A method according to claim 1, wherein said first and said third overlapping regions on the third proximity probe are immediately adjacent each other or spaced 1, 2, 3, 4, 5, 7, 10, 15, 20 or 30 nucleotides apart along the nucleic acid domain of the third proximity probe; and, independently, said second and said fourth overlapping regions on the fourth proximity probe are immediately adjacent each other or spaced 1, 2, 3, 4, 5, 7, 10, 15, 20 or 30 nucleotides apart along the nucleic acid domain of the fourth proximity probe.

8. A method according to claim 7, further comprising filling a gap between the respective overlapping regions by means of enzymatic nucleic acid extension and/or ligation.

9. A method according to claim 1, wherein the detection of the hybridisation product is done by nucleic acid amplification.

10. A method according to claim 1, wherein the respective analyte-binding domains of said proximity probes bind to different epitopes of said analyte.

11. A method according to claim 1, wherein said analyte is selected from the group consisting of proteins, peptides, endosomes, exosomes, organelles, cells, unicellular organisms, viruses, protein aggregates and multi-epitope proteins.

12. A method according to claim 1, wherein each analyte-binding domain is an antibody or fragment thereof, a Protein A-derived affinity molecule, a molecularly imprinted polymer or any affinity binder that can be conjugated to DNA oligonucleotides.

13. A method according to claim 1, wherein the overlapping region of the nucleic acid domain of at least one proximity probe is initially protected by a blocking DNA oligonucleotide or other blocking moiety capable of being released to allow the nucleic acid domain of the proximity probe to hybridise to the nucleic acid domain of another proximity probe to which it is complementary.

14. A method according to claim 1, wherein said overlapping regions independently are 7-13 basepairs in length.

15. A method according to claim 1, wherein said overlapping regions independently are about one helical turn in length.

16. A method according to claim 1, wherein the detection of the hybridization product is done by PCR or by RCA after the hybridisation product is converted to a circularized DNA.

17. A method according to claim 1, wherein the analyte-binding domains are antibodies and the respective antibodies bind to different epitopes of the analyte.

18. A method according to claim 17, wherein the sample is further contacted with an antibody bound to a solid support, wherein the antibody bound to the solid support binds to a different epitope of the analyte than the analyte-binding domain antibodies, and wherein the analyte binds to the solid support via the antibody bound to the solid support.

19. A method according to claim 17, wherein the hybridisation product is converted to a circularized DNA and the circularized DNA is detected by nucleic acid amplification.

\* \* \* \* \*